United States Patent [19]

Kolasa et al.

[11] Patent Number: 5,783,586
[45] Date of Patent: Jul. 21, 1998

[54] HETEROARYLMETHOXYPHENYLTHIOALKYL CARBOXYLATES AS INHIBITORS OF LEUKOTRIENE BIOSYNTHESIS

[75] Inventors: Teodozyj Kolasa, Lake Villa; Clint D. W. Brooks, Libertyville, both of Ill.; David E. Gunn, Hamden, Conn.

[73] Assignee: Abbott Laboratories, Abbott Park, Ill.

[21] Appl. No.: 724,200

[22] Filed: Oct. 1, 1996

[51] Int. Cl.$^6$ ............... C07D 215/14; A61K 31/47
[52] U.S. Cl. ............... 514/311; 514/314; 514/367; 514/375; 514/394; 544/353; 546/174; 548/156; 548/159; 548/179; 548/217; 548/219; 548/305.4; 548/309.7; 548/310.1
[58] Field of Search ............... 546/174; 514/311, 514/314, 255; 544/353

[56] References Cited

U.S. PATENT DOCUMENTS

| | | |
|---|---|---|
| 4,970,215 | 11/1990 | Mohrs et al. ............... 514/311 |
| 5,358,955 | 10/1994 | Brooks et al. ............... 514/311 |
| 5,399,699 | 3/1995 | Kolasa et al. ............... 546/273 |

FOREIGN PATENT DOCUMENTS

| | | |
|---|---|---|
| 399 818 | 11/1990 | European Pat. Off. . |
| WO 89/12628 | 12/1989 | WIPO . |

OTHER PUBLICATIONS

A. J. Mancuso, et al. Oxidation of Long–Chain and Related Alcohols to Carbonyls by Dimethyl Sulfoxide "Activated" by Oxalyl Chloride J. Org. Chem., vol. 43, No. 12, 1978.

O. Mitsunobu, Sunthesis International Journal of Methods in Synthetic Organic Chemistry 1981 No. 1: Jan. 1981.

S. Berge, et al. Pharmaceutical Salts, Journal of Pharm Sciences Jan. 1977 vol. 66 No. 1, Jan. 1977.

T. Rao, et al. Evaluation of 5–Liboxygenase Inhibitors, Zileuton, A–78773 and ICI–D–2138 in an Ionophore (A–23187)Induced Pleural Inflammation Model in the Rat. Life Sciences, vol. 53, PP PL 147–152, 1993.

D. Prescott Methods in Cell Biology Academic Press, 1976.

Primary Examiner—Mukund J. Shah
Assistant Examiner—Deepak R. Rao
Attorney, Agent, or Firm—Frank Z. Yang

[57] ABSTRACT

Compounds having the formula:

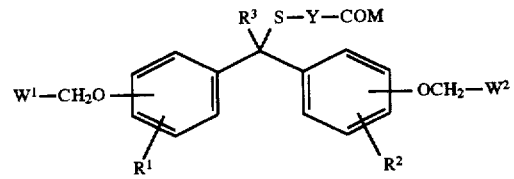

wherein $W^1$ and $W^2$ are independently selected from optionally substituted quinolyl, optionally substituted benzothiazolyl, optionally substituted benzoxazolyl, optionally substituted benzimidazolyl, optionally substituted quinoxalyl, optionally substituted naphthyl; $R^1$ and $R^2$ are independently selected from hydrogen, alkyl, halolalkyl, alkoxy, halogen; $R^3$ is selected from thienyl, furyl, phenyl, naphthyl, benzo[b]thienyl, alkyl, hydroxyl, and hydrogen; Y an alkylene of one to six carbon atoms; and M is selected from (a) a pharmaceutically acceptable metabolically cleavable group, (b) —$OR^4$, (c) —$NR^5R^6$, (d)—$NR^4SO_2R^7$ (e)—NH—Tetrazolyl, and (f) glycinyl; inhibit leukotriene biosynthesis and are useful in the treatment of allergic and inflammatory disease states. Also disclosed are leukotriene biosynthesis inhibiting compositions and a method of inhibiting leukotriene biosynthesis.

8 Claims, No Drawings

HETEROARYLMETHOXYPHENYLTHIOALKYL CARBOXYLATES AS INHIBITORS OF LEUKOTRIENE BIOSYNTHESIS

TECHNICAL FIELD

This invention relates to compounds having activity to inhibit leukotriene biosynthesis, to pharmaceutical compositions comprising these compounds, and to a medical method of treatment. More particularly, this invention relates to bis-heteroarylmethoxyphenylalkyl carboxylate compounds which inhibit leukotriene-biosynthesis, to pharmaceutical compositions comprising these compounds and to a method of inhibiting leukotriene biosynthesis.

BACKGROUND OF THE INVENTION

The leukotrienes are extremely potent substances which produce a wide variety of biological effects, often even when present only in nanomolar to picomolar concentrations. Leukotrienes are important pathological mediators in a variety of diseases. Alterations in leukotriene metabolism have been demonstrated in a number of disease states including asthma, allergic rhinitis, rheumatoid arthritis and gout, psoriasis, adult respiratory distress syndrome, inflammatory bowel disease, endotoxin shock syndrome, atherosclerosis, ischemia induced myocardial injury, and central nervous system pathology resulting from the formation of leukotrienes following stroke or subarachnoid hemorrhage.

Compounds which prevent leukotriene biosynthesis are thus useful in the treatment of disease states such as those listed above in which the leukotrienes play an important pathophysiological role.

The enzyme 5-lipoxygenase catalyzes the first step leading to the biosynthesis of all the leukotrienes and therefore inhibition of this enzyme provides an approach to limit the effects of all the products of this pathway. Agents capable of abrogating the effects of these potent mediators of pathophysiological processes represent a promising class of therapeutic agents (Brooks, D. W., Bell, R. L., and Carter, G. W., in Annual Reports in Medicinal Chemistry, Chapter 8, Pulmonary and Antiallergy Agents, Allen, R. C. ed., Academic Press, 1988).

Toward this end, several new agents have been developed which are useful as leukotriene biosynthesis inhibitors. For example, U.S. Pat. No. 4,970,215 to Mohrs, et al. discloses and claims certain 4-(quinolin-2-yl-methoxy)phenylcycloalkyl acetic acids for inhibition of leukotriene synthesis. European Patent Application 0 349 062 to Zamboni, et al. discloses and claims certain quinolylmethoxyphenyl substituted thioalkanoic acid derivatives having leukotriene biosynthesis inhibitory activity. The publication of Prasit, et al. in "Bioorganic and Medicinal Chemistry Letter, 1: 645–648 describes a new potent and orally active leukotriene synthesis inhibitor, L-674,636 ({[4-(4-chlorophenyl)-1-(4-[2-quinolinylmethoxyphenyl)butyl] thio}acetic acid). U.S. Pat. No. 5,358,955 to Brooks, et al. discloses and claims certain pyridyl-, quinolyl- and naphthylmethoxyphenyl compounds which inhibit lipoxygenase activity. Most recently, U.S. Pat. No. 5,399,699 to Kolasa, et al. discloses and claims certain substituted indole iminooxy derivatives which also act as inhibitors of leukotriene biosynthesis.

SUMMARY OF THE INVENTION

The present invention relates to bis-heteroarylmethoxyphenylalkyl carboxylate compounds, their derivatives and pharmaceutically acceptable salts. The compounds have the formula:

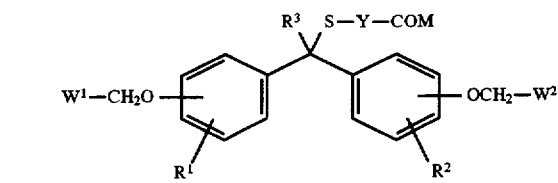

wherein $W^1$ and $W^2$ are selected independently at each occurrence from the group consisting of (a) quinolyl; (b) quinolyl substituted with a substituent selected from the group consisting of (b-1) halogen, (b-2) alkyl of one to six carbon atoms, (b-3) haloalkyl of one to six carbon atoms, and (b-4) alkoxy of one to six carbon atoms; (c) benzothiazolyl; (d) benzothiazolyl substituted with a substituent selected from the group consisting of (d-1) halogen, (d-2) alkyl of one to six carbon atoms, (d-3) haloalkyl of one to six carbon atoms, and (d-4) alkoxy of one to six carbon atoms; (e) benzoxazolyl; (f) benzoxazolyl substituted with a substituent selected from the group consisting of (f-1) halogen, (f-2) alkyl of one to six carbon atoms, (f-3) haloalkyl of one to six carbon atoms, and (f-4) alkoxy of one to six carbon atoms; (g) benzimidazolyl; (h) benzimidazolyl substituted with a substituent selected from the group consisting of (h-1) halogen, (h-2) alkyl of one to six carbon atoms, (h-3) haloalkyl of one to six carbon atoms, and (h-4) alkoxy of one to six carbon atoms; (i) quinoxalyl; (j) quinoxalyl substituted with a substituent selected from the group consisting of (j-1) halogen, (j-2) alkyl of one to six carbon atoms, (j-3) haloalkyl of one to six carbon atoms, and (j-4) alkoxy of one to six carbon atoms, (j-5) pyridyl, and (j-6) pyridyl substituted with a substituent selected from the group consisting of (j-6-a) halogen, (j-6-b) alkyl of one to six carbon atoms, and (j-6-c) alkoxy of one to six carbon atoms; (k) naphthyl; (l) naphthyl substituted with a substituent selected from the group consisting of (l-1) halogen, (l-2) alkyl of one to six carbon atoms, (l-3) haloalkyl of one to six carbon atoms, and (l-4) alkoxy of one to six carbon atoms;

$R^1$ and $R^2$ are independently selected from the group consisting of (a) hydrogen, (b) alkyl of one to six carbon atoms, (c) halolalkyl of one to six carbon atoms, (d) alkoxy of one to six carbon atoms, and (e) halogen;

$R^3$ is selected from the group consisting of (a) thienyl, (b) furyl, (c) phenyl, d) naphthyl, e) benzo[b]thienyl, f) alkyl, g) hydroxyl and h) hydrogen;

Y is an alkylene of one to six carbon atoms; and

M is selected from the group consisting of (a) a pharmaceutically acceptable metabolically cleavable group, (b) —$OR^4$ where $R^4$ is selected from the group consisting of hydrogen and alkyl of one to six carbon atoms, (c)—$NR^5R^6$ where $R^5$ and $R^6$ are independently selected from the group consisting of hydrogen, alkyl of one to six carbon atoms, hydroxy, and alkoxy of one to six carbon atoms, or $R^5$ and $R^6$ taken together define a five- to eight-membered ring, with the proviso that $R^5$ and $R^6$ may not simultaneously be hydroxyl, (d) —$NR^4SO_2R^7$ wherein $R^4$ is as defined above and $R^7$ is alkyl of one to six carbon atoms, (e)—NH—tetrazolyl, and (f) glycinyl.

The present invention also provides pharmaceutical compositions which comprise a therapeutically effective amount of compound as defined above in combination with a pharmaceutically acceptable carrier.

The invention further relates to a method of inhibiting leukotriene biosynthesis in a host mammal in need of such treatment comprising administering to a mammal in need of such treatment a therapeutically effective amount of a compound as defined above.

DETAILED DESCRIPTION

As used throughout this specification and the appended claims, the following terms have the meanings specified.

The term alkyl refers to a monovalent group derived from a straight or branched chain saturated hydrocarbon by the removal of a single hydrogen atom. Alkyl groups are exemplified by methyl, ethyl, n- and iso-propyl, n-, sec-, iso- and tert-butyl, and the like.

The terms alkoxy and alkoxyl denote an alkyl group, as defined above, attached to the parent molecular moiety through an oxygen atom. Representative alkoxy groups include methoxy, ethoxy, propoxy, butoxy, and the like.

The terms alkenyl as used herein refer to monovalent straight or branched chain groups of 2 to 6 carbon atoms containing a carbon-carbon double bond, derived from an alkene by the removal of one hydrogen atom and include, but are not limited to groups such as ethenyl, 1-propenyl, 2-propenyl, 2-methyl-1-propenyl, 1-butenyl, 2-butenyl and the like.

The term alkylene denotes a divalent group derived from a straight or branched chain saturated hydrocarbon containing by the removal of two hydrogen atoms, for example —$CH_2$—, —$CH_2CH_2$—, —$CH(CH_3)CH_2$— and the like.

The term alkenylene denotes a divalent group derived from a straight or branched chain hydrocarbon containing at least one carbon-carbon double bond. Examples of alkenylene include —CH=CH—, —$CH_2$CH=CH—, —C($CH_3$)=CH—, —$CH_2$CH=CH$CH_2$—, and the like.

The terms alkynylene refers to a divalent group derived by the removal of two hydrogen atoms from a straight or branched chain acyclic hydrocarbon group containing at least one carbon-carbon triple bond. Examples of alkynylene include —C≡CH—, —C≡C—$CH_2$—, —C≡C—CH($CH_3$)— and the like.

The term aryl as used herein refers to a monovalent carbocyclic group containing one or more fused or non-fused phenyl rings and includes, for example, phenyl, 1- or 2-naphthyl, 1,2-dihydronaphthyl, 1,2,3,4-tetrahydronaphthyl, and the like.

The term cycloalkyl as used herein refer to a monovalent saturated cyclic hydrocarbon group. Representative cycloalkyl groups include cyclopropyl, cyclobutyl, cyclopentyl, cyclohexyl, cycloheptyl, bicyclo[2.2.1]heptane and the like.

Cycloalkylene denotes a divalent radical derived from a cycloalkane by the removal of two hydrogen atoms.

The term haloalkyl denotes an alkyl group, as defined above, having one, two, or three halogen atoms attached thereto and is exemplified by such groups as chloromethyl, bromoethyl, trifluoromethyl, and the like.

As used throughout this specification and the appended claims, the term "metabolically cleavable group" denotes a moiety which is readily cleaved in vivo from the compound bearing it, which compound after cleavage remains or becomes pharmacologically active. Metabolically cleavable groups form a class of groups reactive with the carboxyl group of the compounds of this invention (where M is —OH) well known to practitioners of the art. They include, but are not limited to such groups as alkanoyl (such as acetyl, propionyl, butyryl, and the like), unsubstituted and substituted aroyl (such as benzoyl and substituted benzoyl), alkoxycarbonyl (such as ethoxycarbonyl), trialkylsilyl (such as trimethyl- and triethysilyl), monoesters formed with dicarboxylic acids (such as succinyl), and the like. Because of the ease with which the metabolically cleavable groups of the compounds of this invention are cleaved in vivo, the compounds bearing such groups act as pro-drugs of other leukotriene biosynthesis inhibitors. The compounds bearing the metabolically cleavable groups have the advantage that they may exhibit improved bioavailability as a result of enhanced solubility and/or rate of absorption conferred upon the parent compound by virtue of the presence of the metabolically cleavable group.

In those instances where M is a hydroxyl, the compounds of the present invention are capable of forming base addition salts. In such instances, the term "pharmaceutically acceptable salts" refers to the relatively nontoxic inorganic and organic base addition salts of compounds of the present invention. These salts can be prepared in situ during the final isolation and purification of the compounds, or by separately reacting the purified carboxyl compound with a suitable base such as the hydroxide, carbonate, or bicarbonate of a pharmaceutically acceptable metal cation or with ammonia, or an organic primary, secondary, or tertiary amine of sufficient basicity to form a salt with the carboxyl functional group of the compounds of this invention.

Representative alkali or alkaline earth metal salts include sodium, lithium, potassium, calcium, magnesium, and the like. Representative organic amines useful for the formation of base addition salts include ethylamine, diethylamine, ethylenediamine, ethanolamine, diethanolamine, piperazine, and the like. (See, for example, S. M. Berge, et al., *J. Pharmaceutical Sciences*, 1977, 66: 1–19, which is incorporated herein by reference).

Similarly, in those instances where the compounds of the present invention possess a heterocyclic ring moiety containing a basic nitrogen atom, the compounds are capable of forming acid addition salts. In such cases, the term "pharmaceutically acceptable salts" also refers to the nontoxic inorganic and organic acid addition salts of compounds of the present invention. These salts can be prepared in situ during the final isolation and purification of the compounds, or by separately reacting the purified compound in its free-base form with a suitable inorganic or organic acid and isolating the salt thus formed. Representative acid addition salts include acetate, adipate, alginate, ascorbate, aspartate, benzenesulfonate, benzoate, bisulfate, borate, butyrate, camphorate, camphersulfonate, citrate, cyclopentanepropionate, digluconate, dodecylsulfate, ethanesulfonate, fumarate, glucoheptonate, glycerophosphate, hemisulfate, heptonate, hexanoate, hydrobromide, hydrochloride, hydroiodide, 2-hydroxyethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, toluenesulfonate, undecanoate, valerate salts, and the like. (See, for example, S. M Berge, et al., *J. Pharmaceutical Sciences*, 1977, 66: 1–19, which is incorporated herein by reference). Said pharmaceutically acceptable acid and base addition salts are also contemplated as falling within the scope of the present invention.

Asymmetric centers may exist in the compounds of the present invention. The present invention contemplates the various stereoisomers and mixtures thereof. Individual stereoisomers of compounds of the present invention are made by synthesis from starting materials containing the chiral centers or by preparation of mixtures of enantiomeric products followed by separation as, for example, by conversion to a mixture of diastereomers followed by separation by recrystallization or chromatographic techniques, or by direct separation of the optical enantiomers on chiral chromatographic columns. Starting compounds of particular stereochemistry are either commercially available or are made by the methods detailed below and resolved by techniques well known in the organic chemical arts.

The preferred compounds of the present invention are those of the above formula, wherein $W^1$ and $W^2$, at each occurrence, are independently selected from the group consisting of optionally substituted quinolyl, benzothiazolyl, naphthyl, and benzimidazoyl. The most preferred compounds of the present invention are those wherein $W^1$ and $W^2$ are the same at each occurrence and are selected from the group consisting of (a) quinolyl; and (b) quinolyl substituted with a substituent selected from the group consisting of (b-1) halogen, (b-2) alkyl of one to six carbon atoms, (b-3) haloalkyl of one to six carbon atoms, and (b-4) alkoxy of one to six carbon atoms.

Representative compounds of the invention include, but are not limited to: 1,1-bis(4-(2-quinolylmethoxy)phenyl) eth-1-ylthioacetic acid, (bis(4-(2-quinolylmethoxy)phenyl)-2-thienyl)methylthioacetic acid, (bis(4-(2-quinolylmethoxy) phenyl)-2-thienyl)methylthioacetic acid sodium salt, bis(4-(2-quinolylmethoxy)phenyl)methylthioacetic acid, (bis(4-(2-quinolylmethoxy)phenyl)-phenyl)methylthioacetic acid, 1,1 -bis(4-(2-quinolymethoxy)phenyl-1-pentylthioacetic acid, (bis(4-(2-quinolylmethoxy)phenyl)-furyl) methylthioacetic acid; (4-(2-benzothiazolylmethoxy) phenyl-4-(2-quinolylmethoxy)phenyl-2-thienyl) methylthioacetic acid, (4-(6-fluoro-2-quinolylmethoxy) phenyl-4-(2-quinolylmethoxy)phenylphenyl) methylthioacetic acid, (4-(1-methyl-2-benzimidazolylmethoxy)phenyl-4-(2-quinolylmethoxy) phenyl-2-thienyl)methylthioacetic acid, (4-(2-benzothiazolylmethoxy)phenyl-4-(2-quinolylmethoxy) phenyl-2-furyl)methylthioacetic acid, 1-(4-(2-naphthylmethoxy)phenyl)-1-(4-(2-quinolylmethoxy) phenyl)-1-ethylthioacetic acid, (bis(4-(2-quinolylmethoxy) phenyl)-2-naphthyl)methylthioacetic acid, (4-(2-naphthylmethoxy)phenyl)-(4-(2-quinolylmethoxy)phenyl)-2-naphthyl)methylthioacetic acid, (2-benzo[b]thienyl-bis(4-(2-quinolylmethoxy)phenyl))methylthioacetic acid, (2-benzo[b]thienyl-4-(1-methyl-2-benzimidazolylmethoxy) phenyl-4-(2-quinolylmethoxy)phenyl)methylthioacetic acid (bis(4-(2-quinolylmethoxy)phenyl)-2-thienyl)methylthio-3-propionic acid, (bis(4-(2-quinolylmethoxy)phenyl)-2-thienyl)methylthio -2-propionic acid; 4-(2-benzo[b] thienylmethoxy)phenyl-bis(4-(2-quinolylmethoxy)phenyl)-methylthio-3-propionic acid, (4-(2-benzo[b]thienyl-4-(2-naphthylmethoxy)phenyl-4-(2-quinolylmethoxy)phenyl) methylthio-3-propionic acid, (bis(4-(2-quinolylmethoxy) phenyl)-2-thienyl)methylthio-2-benzoic acid, (4-(2-benzothiazolylmethoxy)phenyl-4-(2-quinolylmethoxy) phenyl)-methylthio-2-benzoic acid, 1-(bis(4-(2-quinolylmethoxy)phenyl)-1-ethylthio-2-benzoic acid; and 1-(4-(2-naphthylmethoxy)phenyl-4-(2-quinolylmethoxy) phenyl)- 1-ethylthio-2-benzoic acid.

Pharmaceutical Compositions

The present invention also provides pharmaceutical compositions which comprise compounds of the present invention formulated together with one or more non-toxic pharmaceutically acceptable carriers. The pharmaceutical compositions may be specially formulated for oral administration in solid or liquid form, for parenteral injection, or for rectal administration.

The pharmaceutical compositions of this invention can be administered to humans and other animals orally, rectally, parenterally, intracisternally, intravaginally, intraperitoneally, topically (as by powders, ointments, or drops), bucally, or as an oral or nasal spray. The term "parenteral" administration as used herein refers to modes of administration which include intravenous, intramuscular, intraperitoneal, intrasternal, subcutaneous and intraarticular injection and infusion.

Pharmaceutical compositions of this invention for parenteral injection comprise pharmaceutically acceptable sterile aqueous or nonaqueous solutions, dispersions, suspensions or emulsions as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol, and the like), and suitable mixtures thereof, vegetable oils (such as olive oil), and injectable organic esters such as ethyl oleate. Proper fluidity can be maintained, for example, by the use of coating materials such as lecithin, by the maintenance of the required particle size in the case of dispersions, and by the use of surfactants.

These compositions may also contain adjuvants such as preservative, wetting agents, emulsifying agents, and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents such as sugars, sodium chloride, and the like. Prolonged absorption of the injectable pharmaceutical form may be brought about by the inclusion of agents which delay absorption such as aluminum monostearate and gelatin.

In some cases, in order to prolong the effect of the drug, it is desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly (orthoesters) and poly(anhydrides). Depot injectable formulations are also prepared by entrapping the drug in liposomes or microemulsions which are compatible with body tissues.

The injectable formulations can be sterilized, for example, by filtration through a bacterial-retaining filter, or by incorporating sterilizing agents in the form of sterile solid compositions which can be dissolved or dispersed in sterile water or other sterile injectable medium just prior to use.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

The active compounds can also be in micro-encapsulated form, if appropriate, with one or more of the above-mentioned excipients.

Liquid dosage forms for oral administration include pharmaceutically acceptable emulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, and perfuming agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar, and tragacanth, and mixtures thereof.

Compositions for rectal or vaginal administration are preferably suppositories which can be prepared by mixing the compounds of this invention with suitable non-irritating excipients or carriers such as cocoa butter, polyethylene glycol or a suppository wax which are solid at room temperature but liquid at body temperature and therefore melt in the rectum or vaginal cavity and release the active compound.

Compounds of the present invention can also be administered in the form of liposomes. As is known in the art, liposomes are generally derived from phospholipids or other lipid substances. Liposomes are formed by mono- or multi-lamellar hydrated liquid crystals that are dispersed in an aqueous medium. Any non-toxic, physiologically acceptable and metabolizable lipid capable of forming liposomes can be used. The present compositions in liposome form can contain, in addition to a compound of the present invention, stabilizers, preservatives, excipients, and the like. The preferred lipids are the phospholipids and the phosphatidyl cholines (lecithins), both natural and synthetic.

Methods to form liposomes are known in the art. See, for example, Prescott, Ed., *Methods in Cell Biology*, Volume XIV, Academic Press, New York, N.Y. (1976), p. 33, et seq.

Dosage forms for topical administration of a compound of this invention include powders, sprays, ointments and inhalants. The active compound is mixed under sterile conditions with a pharmaceutically acceptable carrier and any needed preservatives, buffers, or propellants which may be required. Opthalmic formulations, eye ointments, powders and solutions are also contemplated as being within the scope of this invention.

Actual dosage levels of active ingredients in the pharmaceutical compositions of this invention may be varied so as to obtain an amount of the active compound(s) that is effective to achieve the desired therapeutic response for a particular patient, compositions, and mode of administration. The selected dosage level will depend upon the activity of the particular compound, the route of administration, the severity of the condition being treated, and the condition and prior medical history of the patient being treated. However, it is within the skill of the art to start doses of the compound at levels lower than required for to achieve the desired therapeutic effect and to gradually increase the dosage until the desired effect is achieved.

Generally dosage levels of about 1 to about 50, more preferably of about 5 to about 20 mg of active compound per kilogram of body weight per day are administered orally to a mammalian patient. If desired, the effective daily dose may be divided into multiple doses for purposes of administration, e.g., two to four separate doses per day.

Preparation Of Compounds Of This Invention

The preparation of compounds of this invention is outlined in Scheme 1 and described as follows. Reaction of a 4,4'-dihydroxybenzophenone derivative I with the requisite heteroarylmethylhalide(s) of formula W—CH$_2$X, where X is Cl, Br, or I and W is W$^1$ and/or W$^2$, which are as defined above, in the presence of a suitable base such as K$_2$CO$_3$ provides the desired intermediate II. Treatment of compound II with metallo-organic derivatives R$^3$M, preferably organolithium compounds, gives adducts of formula III. Intermediates of formula III are reacted with mercapto-alkylester, HS—Y—COOR$^8$ where R$^8$ is alkyl and Y is as defined previously, in the presence of a suitable acid, to give the adduct of formula IV. Hydrolysis of the ester, for example using aqueous alkali, provides compounds of formula V wherein R$^8$ is H.

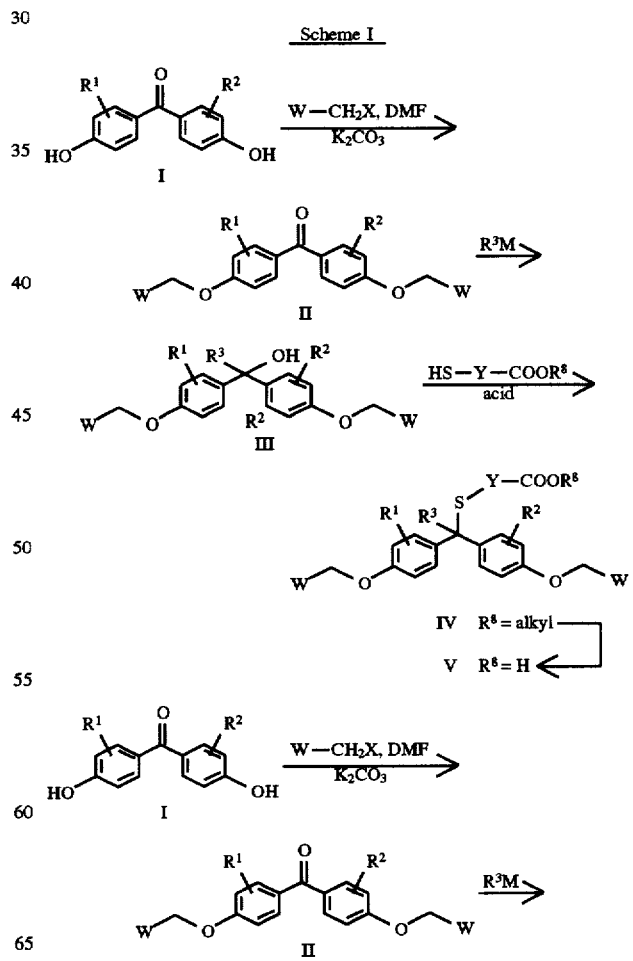

-continued
Scheme I

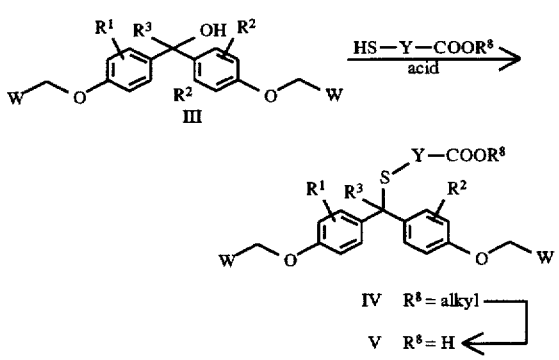

The foregoing may be better understood by reference to the following Examples which are provided for illustration and are not intended to limit the scope of the invention as it is defined by the appended claims. In the Examples below, the starting materials are the intermediates of formula II in Scheme 1 above, prepared from the corresponding 4,4'-dihydroxybenzophenone of formula I and heteroarylmethylhalide(s) of formula W—CH$_2$X by the methods well known to the persons of ordinary skill in the art.

EXAMPLE 1

Preparation of 1,1-bis(4-(2-quinolylmethoxy)phenyl)eth-1-ylthioacetic acid

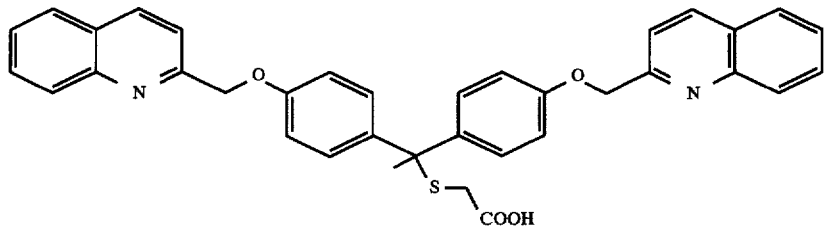

To a solution of 4,4'-di(2-quinolylmethoxy)benzophenone (992 mg, 2 mmol) in THF (20 mL) at −78° C. was added methylmagnesium bromide (3M solution in ethyl ether, 0.8 mL, 2.4 mmol) and the resulting mixture was stirred at room temperature for 12 hours. The mixture was then quenched with saturated aqueous NH$_4$Cl and extracted with ethyl acetate. The extract was washed with water, brine, dried with anhydrous MgSO$_4$ and concentrated in vacuo. The residue was chromatographed (silica gel, methylene chloride-ethyl acetate 4:1) to afford 920 mg of 1,1-bis(4-(2-quinolylmethoxy)phenyl)ethanol.

A mixture of 1,1-bis(4-(2-quinolylmethoxy)phenylethanol (300 mg, 0.6 mmol) and ethyl thioglycolate (0.1 mL, 0.7 mmol) in methylene chloride (15 mL) at 0° C. was treated with boron trifluoride etherate (0.24 mL, 2 mmol) and the mixture was left at 0° C. for additional 1 hour. The mixture was then quenched with saturated solution of NH$_4$Cl and extracted with methylene chloride. The extract was dried with anhydrous MgSO$_4$ and concentrated in vacuo. The residue was chromatographed (silica gel, 9:1 methylene chloride-ethyl acetate) to provide 220 mg of ethyl ester of 1,1-bis(4-(2-quinolylmethoxy)phenyl)eth-1-ylthioacetic acid.

1N sodium hydroxide (0.5 mL) was added to a solution of ethyl 1,1-bis(4-(2-quinolylmethoxy)phenyl)eth-1-ylthioacetate from above in dioxane (10 mL) and ethanol (5 mL), and the resulting mixture was stirred at ambient temperature for 3 hours. The organics were removed in vacuo, the residue was diluted with water and acidified to pH 3. The solid was filtered, washed with water, dried under reduced pressure and recrystallized from methylene chloride-hexane to provide 170 mg of the title compound: mp 92°–94° C.; $^1$H NMR (300 MHz, DMSO-d$_6$)δ 2.00 (s, 3 H), 3.32 (s, 2 H), 5.34 (s, 4 H), 7.02 (d, J=9 Hz, 4 H), 7.30 (d, J=9 Hz, 4 H), 7.63 (m, 4 H), 7.78 (m, 2 H), 8.00 (m, 4 H), 8.41 (d, J=8 Hz, 2 H); MS (DCI-NH$_3$) m/z 587 (M+H)$^+$. Anal. Calc'd. for C$_{36}$H$_{30}$N$_2$O$_4$S: C, 73.70; H, 5.15; N, 4.77. Found: C, 74.24; H, 5.28; N, 4.34.

EXAMPLE 2

Preparation of (bis(4-(2-quinolylmethoxy)phenyl)-2-thienyl)methylthioacetic acid

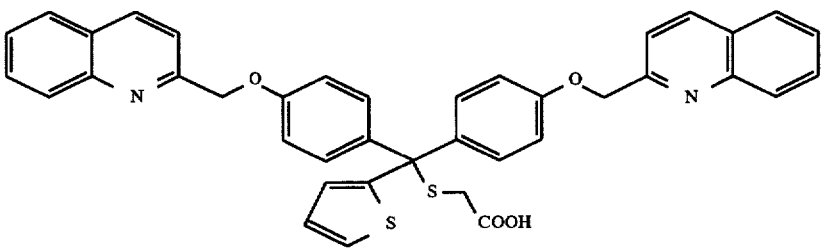

To a solution of 4,4'-bis(2-quinolylmethoxy)benzophenone (7.44 g, 15 mmol) in THF (75 mL) was added 2-thienyllithium (16 mL of 1M solution in THF, 16 mmol) and the resulting mixture was allowed to warm to the ambient temperature (~2 hours). A saturated solution of NH₄Cl was added and the mixture was extracted with ethyl acetate, washed with water, brine, dried (MgSO₄) and concentrated in vacuo. The residue was purified by chromatography (silica gel, 4:1 CH₂Cl₂/EtOAc) to provide 5.8 g (65%) of (bis(4-(2-quinolylmethoxy)phenyl)-2-thienyl)methanol. Recovered was 760 mg (10%) of starting material.

A mixture of alcohol intermediate from above (2.90 g, 5 mmol) and ethyl mercaptoacetate (0.6 mL, 5.3 mmol) in acetic acid (100 mL) and CHCl₃ (20 mL) was treated with BF₃: Et₂O (1.75 ml, 15 mmol) and the reaction mixture was stirred at room temperature for 1 hour. The mixture was poured slowly into saturated aqueous NaHCO₃ and extracted with ethyl acetate, washed with water, 10% NaHCO₃, brine, dried (MgSO₄) and concentrated in vacuo. The residue was purified by chromatography (silica gel, 9:1 CH₂Cl₂/Et₂O) to afford 1.8 g (53%) of ester intermediate.

To a solution of the ester intermediate from above (2.1 g, 3 mmol) in dioxane (50 mL) and ethanol (15 mL) was added 1N NaOH (3.5 mL, 3.5 mmol) and the resulting solution was stirred at room temperature for 3 hours. Water (40 mL) was added and the organics were removed in vacuo. The water solution was acidified to pH 3 with 10% citric acid, the solid was filtered and recrystallized from dioxane-water to provide 1.9 g (97%) of the desired product. mp 99°–101° C.; ¹H NMR (300 MHz, DMSO-d₆) δ 3.06 (s, 2 H), 5.35 (s, 4 H), 6.85 (d-d, J=5 and 2 Hz, 1 H), 6.98 (d-d, J=5 and 3 Hz, 1 H), 7.06 (d, J=9 Hz, 4 H), 7.26 (d, J=9 Hz, 4 H), 7.48 (d-d, J=5 and 2 Hz, 1 H), 7.62 (m, 2 H), 7.69 (d, J=8 Hz, 2 H), 7.79 (m, 2 H), 8.01 (m, 4 H), 8.42 (d, J=8 Hz, 2 H); MS (FAB(+)) m/z 655 (M+H)⁺; MS (FAB(−)) m/z 653 (M−H)⁻. Anal. Calc'd. for C₃₉H₃₀N₂O₄S₂×0.75 H₂O: C, 70.09; H, 4.68; N, 4.19. Found: C, 70.06; H, 4.73; N, 3.89.

EXAMPLE 3

Preparation of (bis(4-(2-quinolylmethoxy)phenyl)-2-thienyl)methylthioacetic acid sodium salt

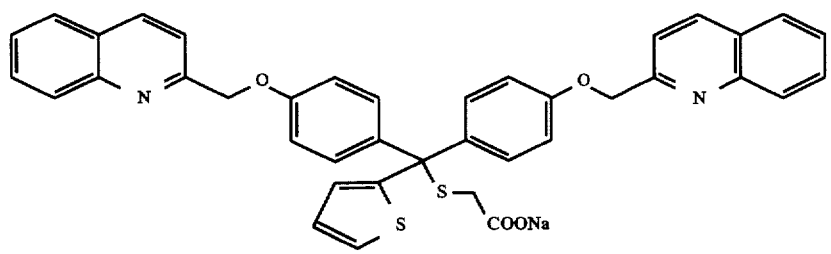

The desired material was prepared by neutralization of the product of Example 2 according to standard procedures. mp >80° C. (decomp); ¹H NMR (300 MHz, DMSO-d₆) δ 2.70 (s, 2 H), 5.34 (s, 4 H), 6.88 (d-d, 1 H, J=1.5 and 4.5 Hz), 6.93 (d-d, 1 H, J=3 and 4.5 Hz), 7.03 (d, 4 H, J=9 Hz), 7.26 (d, 4 H, J=9 Hz), 7.40 (d-d, 1 H, J=1.5 and 4.5 Hz), 7.62 (m, 2 H), 7.70 (d, 2 H, J=8 Hz), 7.79 (m, 2 H), 8.01 (m, 4 H), 8.42 (d, 2 H, J=8 Hz); MS (FAB(+)) m/z 677 (M+H)⁺, 699 (M+Na)⁺; FAB(−) m/z 653 (M−Na)⁻. Anal. Calc'd. for C₃₉H₂₉N₂O₄S₂Na×1.5 H₂O: C, 66.55; H, 4.58; N, 3.98; Found: C, 66.53; H, 4.33; N, 3.87.

EXAMPLE 4

Preparation of bis(4-(2-quinolylmethoxy)phenyl)methylthioacetic acid

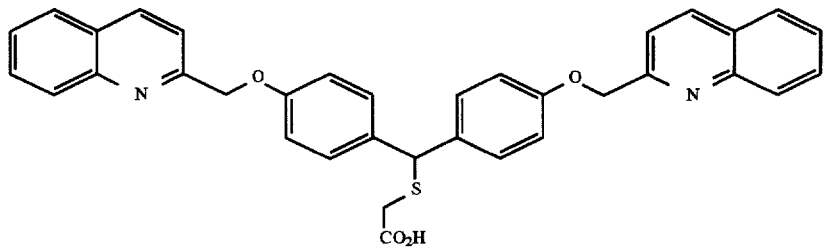

To a bis(4-(2-quinolylmethoxy)phenyl)methanol (0.75 g, 1.51 mmol) in methylene chloride/chloroform (1:1) mixture (8 mL) was added ZnI₂ (0.601 g, 1.91 mmol). After 10 minutes ethyl 2-mercaptoacetate (0.239 ml, 2.18 mmol) was added and the mixture was allowed to stir for 14 hours at room temperature. Water was added and the product was extracted with CHCl₃ (2×). The organic layer was washed with water, brine, dried over MgSO₄, filtered and concentrated in vacuo. The residue was purified by chromatography (silica gel, 2:1 Hexane/EtOAc) to provide 650 mg of bis(4-(2-quinolylmethoxy)phenyl)methylthioacetic acid ethyl ester.

The ester (0.609 g, 1.01 mmol) was dissolved in a mixture of EtOH:THF (15:5) (20 mL) at room temperature and 1N NaOH (1.27 mL, 1.27 mmol) was added. The reaction mixture was refluxed for 15 hours and H₂O (50 mL) was added to the mixture. 10% Citric acid was added to pH 3 and the product was extracted with EtOAc (2×). The organic layer was washed with water, brine, dried over MgSO₄ and concentrated in vacuo. The residue was triturated with hexanes and the solid was filtered to give 300 mg of the title compound as a white powder: mp 175°–180° C.; ¹H NMR (300 MHz, DMSO-d₆) δ 3.02 (s, 2 H), 5.29 (s, 1 H), 5.34 (s, 4 H), 7.03 (d, J=9 Hz, 4 H), 7.33 (d, J=9 Hz, 4 H), 7.63 (m, 4 H), 7.79 (m, 2 H), 8.00 (m, 4 H), 8.41 (d, J=9 Hz, 1 H), 12.51 (br s, 1 H); MS (DCI-NH₃) m/z 573 (M+H)⁺. Anal. Calc'd. for C₃₅H₂₈N₂O₄S×1.1 H₂O: C, 70.95; H 5.14; N, 4.73. Found: C, 71.08; H, 5.11; N, 4.41.

EXAMPLE 5

Preparation of (bis(4-(2-quinolylmethoxy)phenyl)-phenyl)methylthioacetic acid

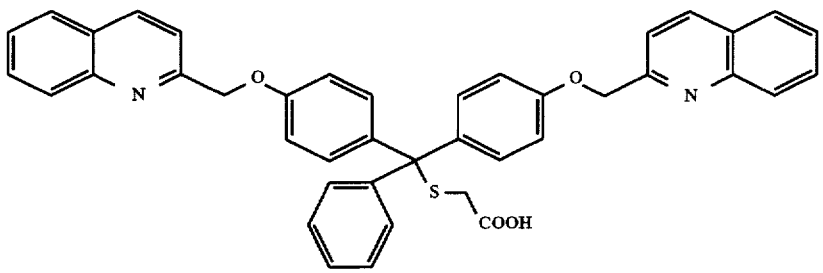

To a solution of 4-(2-quinolylmethoxy)phenyl ketone (0.520 g, 1.05 mmol) in anhydrous THF (10 mL) at −78° C. phenyl lithium (0.873 mL, 1.57 mmol) was added and the reaction mixture was allowed to warm to room temperature. Water was then added to the reaction mixture and the product was extracted with EtOAc (233). The organic layer was washed with water, brine, dried over $MgSO_4$, filtered and concentrated in vacuo. The residue was triturated with $Et_2O$ to give 400 mg of (bis(4-(2-quinolylmethoxy)phenyl)-phenyl)methanol as a cream solid.

The title compound was prepared according to the procedure of Example 4, substituting (bis(4-(2-quinolylmethoxy)phenyl)-phenyl)methanol for bis(4-(2-quinolylmethoxy)phenyl)methanol. mp 89°–91° C.; $^1H$ NMR (500 MHz, DMSO-$d_6$) δ 2.85 (s, 2 H) 5.34 (s, 4 H), 7.04 (d, J=10 Hz, 4 H), 7.23 (d, J=10 Hz, 4 H), 7.25 (m, 1 H), 7.32 (m, 4 H), 7.61 (t, J=7.50 Hz, 2 H), 7.69 (d, J=10 Hz, 2 H), 7.78 (t, J=7.50 Hz, 2 H), 8.01 (dd, J=11.50, 7.50 Hz, 4 H), 8.42 (d, J=10 Hz, 2 H); MS (FAB(−)) m/z 647 (M−H)$^-$. Anal. Calc'd. for $C_{41}H_{32}N_2O_4S \times 0.25\ H_2O$: C, 75.38; H, 5.01; N, 4.28. Found: C, 75.31; H, 4.97; N, 4.20.

EXAMPLE 6

Preparation of 1,1-bis(4-(2-quinolylmethoxy)phenyl-1-pentylthioacetic acid

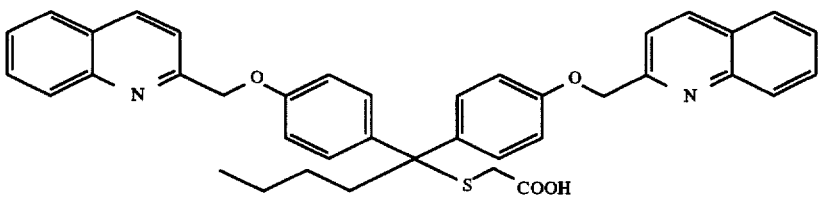

The desired material was prepared according to the method of Example 1, except substituting n-butyllithium for methylmagnesium bromide.

EXAMPLE 7

Preparation of (bis(4-(2-quinolylmethoxy)phenyl)-furyl)methylthioacetic acid

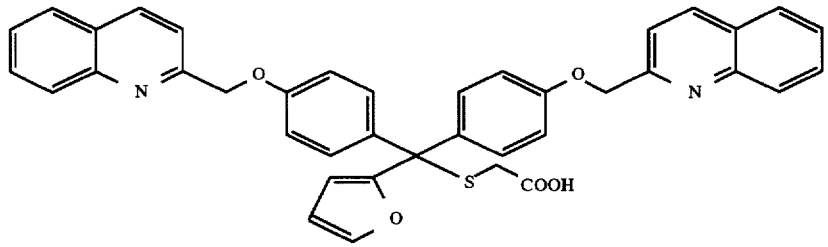

The desired material was prepared according to the method of Example 1, except substituting 2-furyllithium for methylmagnesium bromide.

EXAMPLE 8

Preparation of (4-(2-benzothiazolylmethoxy)phenyl-4-(2-quinolylmethoxy)penyl-2-thienyl) methylthioacetic acid

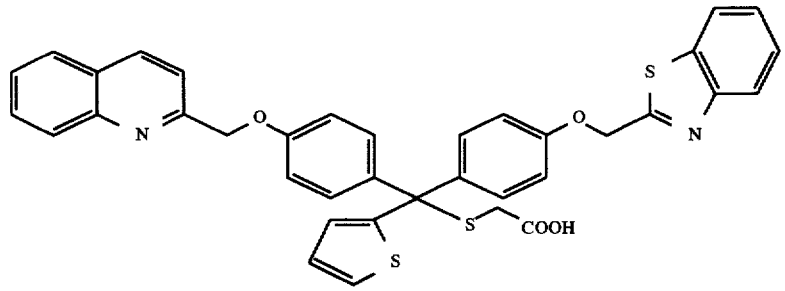

The desired material was prepared according to the procedure of Example 2, except starting with 4-(2-quinolylmethoxyphenyl)-4-(2-benzothienylmethoxyphenyl) ketone.

EXAMPLE 9

Preparation of (4-(6-fluoro-2-quinolylmethoxy) phenyl-4-(2-quinolylmethoxy)phenyl-phenyl) methylthioacetic acid

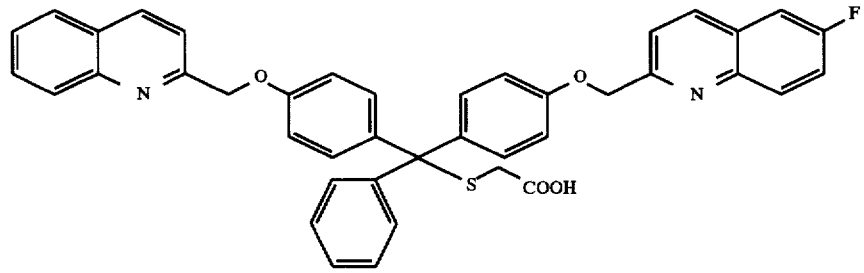

The desired material was prepared according to the method of Example 5, except starting with 4-(2-quinolylmethoxyphenyl)-4-(6-fluoro-2-quinolylmethoxyphenyl) ketone.

EXAMPLE 10

Preparation of (4-(1-methyl-2-benzimidazolylmethoxy)phenyl-4-(2-quinolylmethoxy)phenyl-2-thienyl)methylthioacetic acid

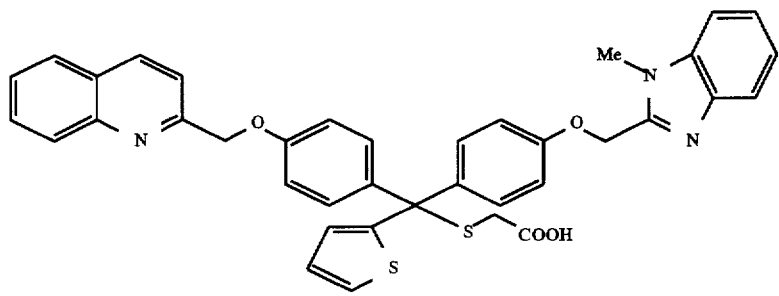

The desired material was prepared according to the method of Example 2 excepting starting with 4-(2-quinolylmethoxyphenyl)-4-(2-benzimidazoylmethoxyphenyl) ketone.

EXAMPLE 11

Preparation of (4-(2-benzothiazolylmethoxy)phenyl-4-(2-quinolylmethoxy)phenyl-2-furyl) methylthioacetic acid

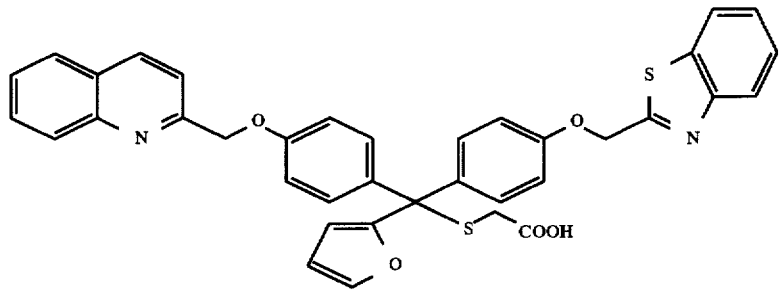

The desired material was prepared according to the method of Example 7, except starting with 4-(2-quinolylmethoxyphenyl)-4-(2-benzothiazoylmethoxyphenyl) ketone.

EXAMPLE 12

Preparation of 1-(4-(2-naphthylmethoxy)phenyl)-1-(4-(2-quinolylmethoxy)phenyl)-1-ethylthioacetic acid

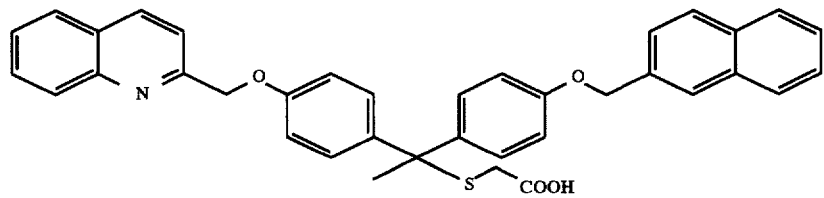

The desired material was prepared according to the method of Example 1, except starting with 4-(2- quinolylmethoxyphenyl)-4-(2-naphthylmethoxyphenyl) ketone.

EXAMPLE 13

Preparation of (bis(4-(2-quinolylmethoxy)phenyl)-2-naphthyl)methylthioacetic acid

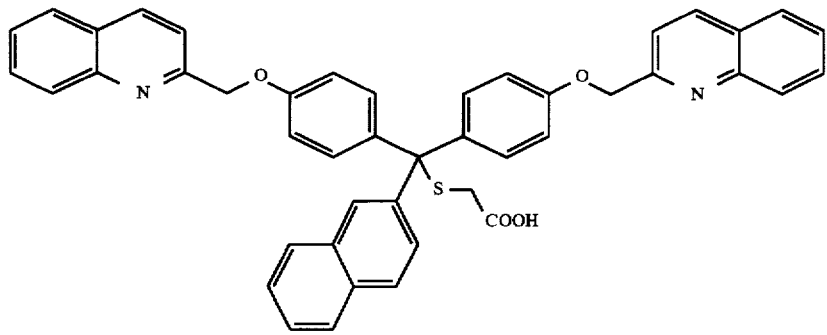

The desired material was prepared according to the procedure of Example 1, except substituting 2-naphthyllithium for methylmagnesium bromide.

EXAMPLE 14

Preparation of (4-(2-naphthylmethoxy)phenyl)-(4-(2-quinolylmethoxy)phenyl)-2-naphthyl) methylthioacetic acid

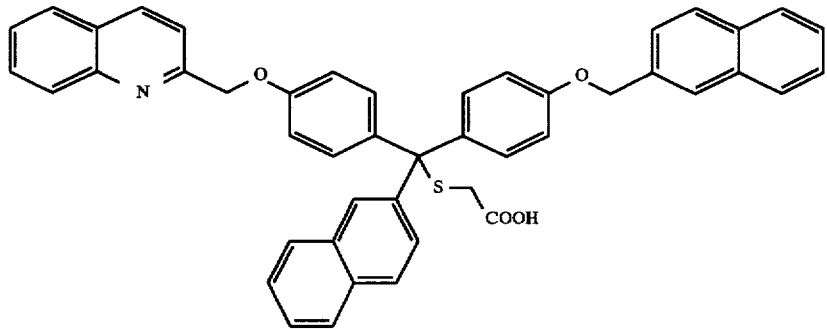

The desired material was prepared according to the procedure of Example 1, except starting with 4-(2-naphthylmethoxy)phenyl 4-(2-quinolylmethoxy)phenyl ketone and substituting 2-naphthyllithium for methylmagnesium bromide.

EXAMPLE 15

Preparation of (2-benzo[b]thienyl-bis(4-(2-quinolylmethoxy)phenyl))methylthioacetic acid

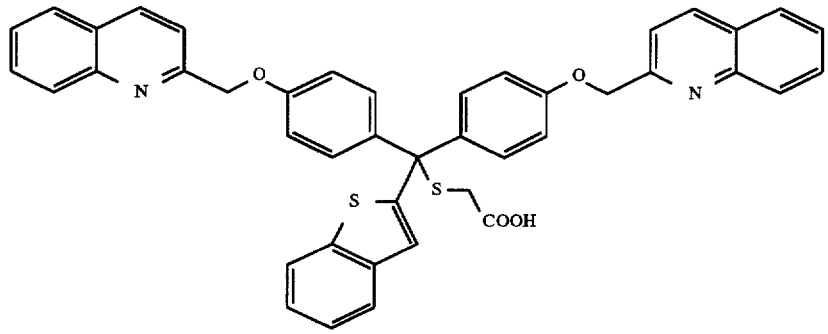

The desired material was prepared according to the procedure of Example 2, except substituting 2-benzo[b]thienyllithium for 2-thienyllithium.

EXAMPLE 16

Preparation of (2-benzo[b]thienyl-4-(1-methyl-2-benzimidazolylmethoxy) phenyl-4-(2-quinolylmethoxy)phenyl)methylthioacetic acid

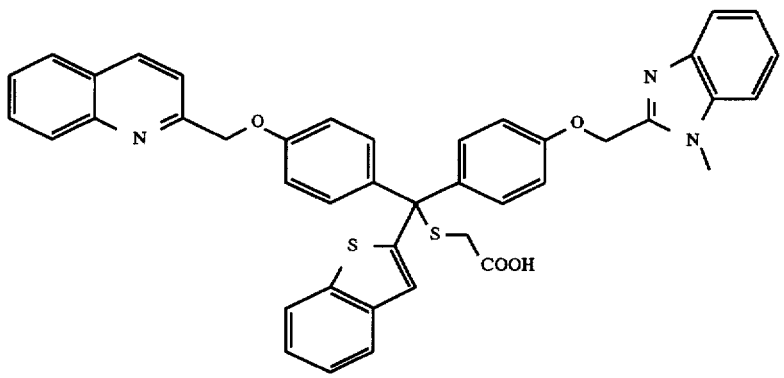

The desired material was prepared according to the procedure of Example 2, except starting with 4-(2-benzimidazolylmethoxy-1-methyl)phenyl 4-(2-quinolylmethoxy)phenyl ketone and substituting 2-benzo[b]thienyllithium for 2-thienyllithium.

EXAMPLE 17

Preparation of (bis(4-(2-quinolylmethoxy)phenyl)-2-thienyl)methylthio-3-propionic acid

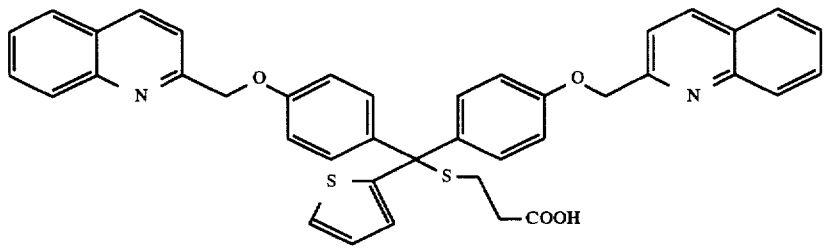

The desired material was prepared according to the procedure of Example 2, except substituting 3-mercaptopropionic acid for mercaptoacetic acid.

EXAMPLE 18

Preparation of (bis(4-(2-quinolylmethoxy)phenyl)-2-thienyl)methylthio -2-propionic acid

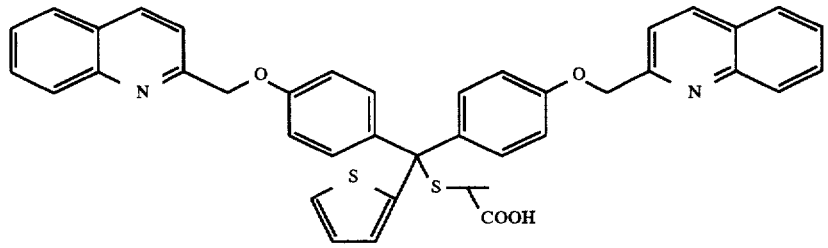

The desired material was prepared according to the procedure of Example 2, except substituting 2-mercaptopropionic acid for mercaptoacetic acid.

EXAMPLE 19

Preparation of (4-(2-benzo[b]thienylmethoxy)phenyl-bis(4-(2-quinolylmethoxy)phenyl)methylthio-3-propionic acid

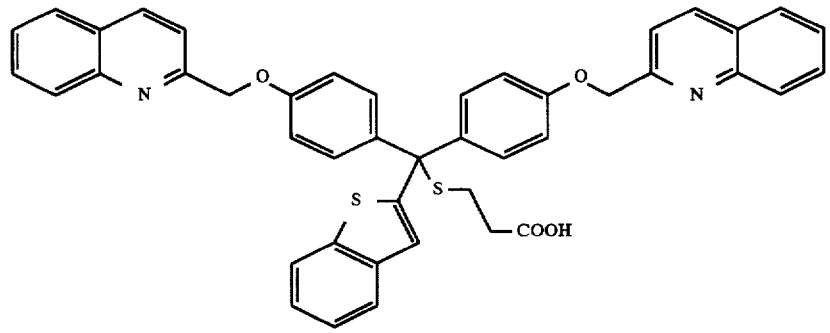

The desired material was prepared according to the procedure of Example 2, except substituting 2-benzo[b]tienyllithium for 2-thienyllithium and 3-mercaptopropionic acid for mercaptoacetic acid.

EXAMPLE 20

Preparation of (4-(2-benzo[b]thienyl-4-(2-naphthylmethoxy)phenyl-4-(2-quinolylmethoxy)phenyl)methylthio-3-propionic acid

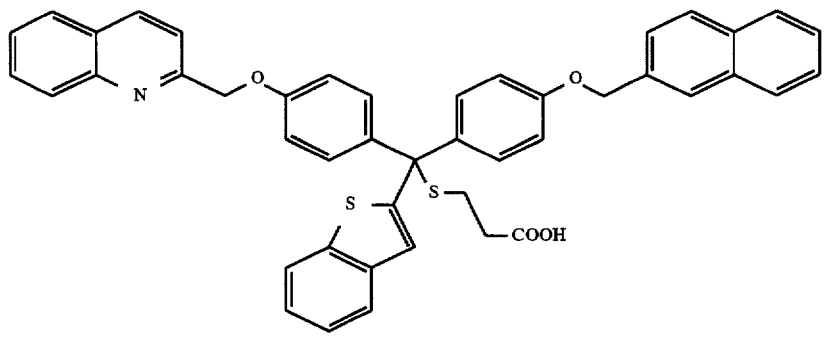

The desired material was prepared according to the procedure of Example 19, except starting with 4-(2-naphthylmethoxy)phenyl 4-(2-quinolylmethoxy)phenyl ketone.

EXAMPLE 21

Preparation of (bis(4-(2-quinolylmethoxy)phenyl)-2-thienyl)methylthio-2-benzoic acid

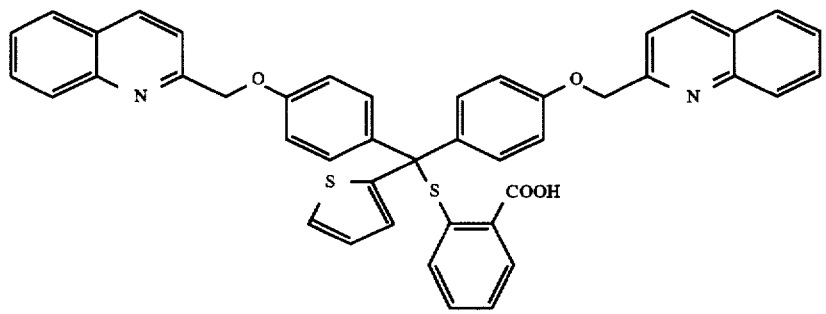

The desired material was prepared according to the procedure of Example 2, except substituting 2-mercaptobenzoic acid for mercaptoacetic acid.

EXAMPLE 22

Preparation of (4-(2-benzothiazolylmethoxy)phenyl-4-(2-quinolylmethoxy)phenyl)methylthio-2-benzoic acid

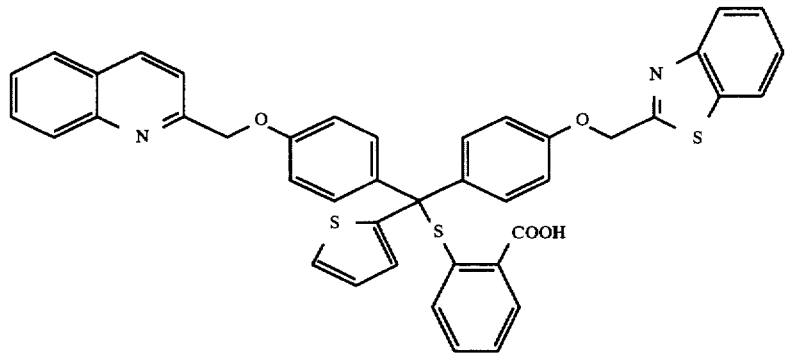

The desired material was prepared according to the procedure of Example 21, except starting with 4-(2-benzothiazolylmethoxy)phenyl 4-(2-quinolylmethoxy) phenyl ketone.

EXAMPLE 23

Preparation of 1-(bis(4-(2-quinolylmethoxy)phenyl)-1-ethylthio-2-benzoic acid

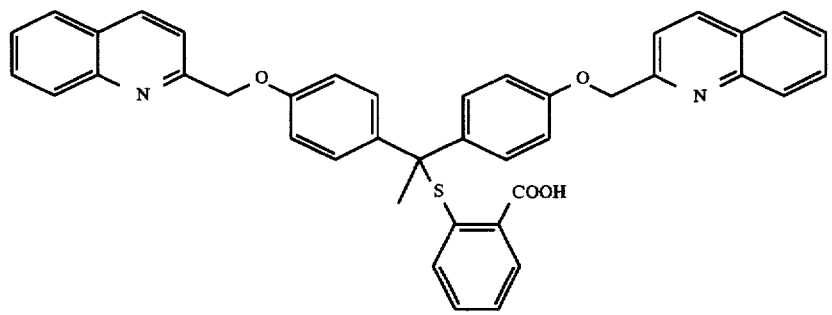

The desired material was prepared according to the procedure of Example 1, except substituting 2-mercaptobenzoic acid for mercaptoacetic acid.

EXAMPLE 24

Preparation of 1-(4-(2-naphthylmethoxy)phenyl-4-(2-quinolylmethoxy)phenyl)-1-ethylthio-2-benzoic acid

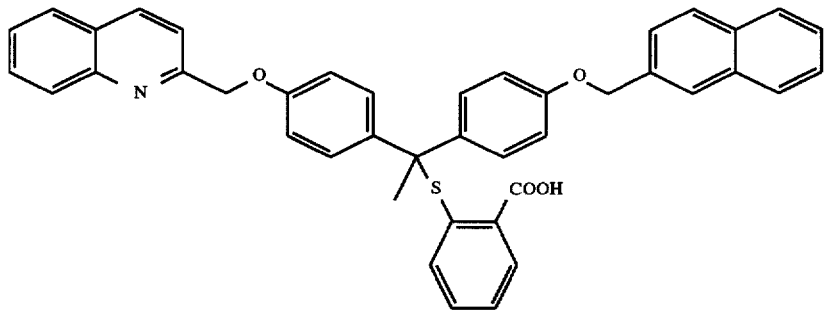

The desired material was prepared according to the procedure of Example 23, except starting with 4-(2-naphthylmethoxy)phenyl 4-(2-quinolylmethoxy)phenyl ketone.

Lipoxygenase Inhibition Determination in vitro

Inhibition of leukotriene biosynthesis was evaluated in vitro using an assay involving calcium ionophore-induced $LTB_4$ expressed in human polymorphonuclear leukocytes (PMNL). Human PMNL isolated from heparinized (20 USP units/mL) venous blood (25 mL) obtained from healthy volunteers was layered over an equal volume of Ficoll-Hypaque Mono-Poly Resolving Medium (ICN Flow, Costa Mesa, Calif.) and centrifugated at 400 × g for 40 minutes at 20° C. The PMNL was collected, erythrocytes lysed and washed 2× and suspended at $1.0 \times 10^7$ cells/ml in Earle's balanced salt solution with 17 mM Earle's HEPES. Aliquots of the cell suspension were preincubated with test compounds dissolved in DMSO (final concentration <2%) for 15 minutes and stimulated with calcium ionophore (final concentration 8.3 μM) for 10 minutes at 37° C. Incubations were stopped with the addition of two volumes of ice-cold methanol followed by centrifuging the cell suspensions at 4° C. for 10 minutes at 450 × g. The amount of $LTB_4$ in the methanol extract was analyzed by enzyme-linked immunoassay or by HPLC analysis.

The compounds of this invention inhibit leukotriene biosynthesis as shown by the data for representative Example 1 with an $IC_{50}$ of 0.23 μM.

Lipoxygenase Inhibition Determination in vivo

Inhibition of leukotriene biosynthesis in vivo was evaluated using the Ionophore A32187-Induced Rat Plueral Inflammation Model. Pleural inflammation was induced in male rats following the method of Rao, et al (Rao, T. S., Currie, J. L., Shaffer, A. F., Isakson, P. C., (1993) Evaluation of 5-lipoxygenase Inhibitors, Zileuton, A-78773 and ICI D-2138 in an Ionophore (A-23187) Induced Pleural Inflammation Model in the Rat, *Life Sciences*, 53: 147 (1993)). Rats were dosed with experimental compounds in 0.2% methocel one hour prior to the intrapleural injection of the calcium ionophore, A23187. The rats where lightly anesthetized with Pentrane (Abbott Laboratories) and injected intrapleurally with 0.5 ml of 2% ethanol in injectable saline (Abbott Laboratories) containing 20 μg of A23187 (Cal BioChem-Novabiochem). Thirty minutes later the animals were euthanised and the pleural cavities lavaged with ice cold saline (Abbott Laboratories). The lavage fluid was then added to ice cold methanol (final methanol concentration 30%) to lyse cells and precipitate protein. Eicosanoids were determined by enzyme immunoassay by standard methods.

The compounds of this invention inhibit leukotriene biosynthesis as shown by the data for representative Example 1 with an $ED_{50}$ of 1.1 mg/kg.

What is claimed is:

1. A compound of formula:

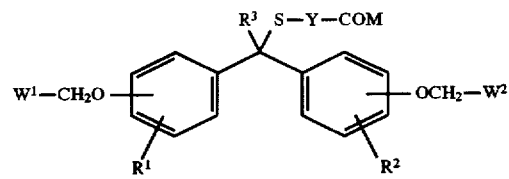

or a pharmaceutically acceptable salt thereof;
  wherein $W^1$ and $W^2$ are independently selected from the group consisting of
  (a) quinolyl;
  (b) quinolyl substituted with a substituent selected from the group consisting of
    halogen,
    alkyl of one to six carbon atoms,
    haloalkyl of one to six carbon atoms, and
    alkoxy of one to six carbon atoms;
  (c) benzothiazolyl;
  (d) benzothiazolyl substituted with a substituent selected from the group consisting of
    halogen,
    alkyl of one to six carbon atoms,
    haloalkyl of one to six carbon atoms, and
    alkoxy of one to six carbon atoms,
  (e) benzoxazolyl;
  (f) benzoxazolyl substituted with a substituent selected from the group consisting of
    halogen,
    alkyl of one to six carbon atoms,
    haloalkyl of one to six carbon atoms, and
    alkoxy of one to six carbon atoms;
  (g) benzimidazolyl;
  (h) benzimidazolyl substituted with a substituent selected from the group consisting of
    halogen,
    alkyl of one to six carbon atoms,
    haloalkyl of one to six carbon atoms, and

31 alkoxy of one to six carbon atoms;
(i) quinoxalyl;
(j) quinoxalyl substituted with a substituent selected from the group consisting of
  halogen,
  alkyl of one to six carbon atoms,
  haloalkyl of one to six carbon atoms,
  alkoxy of one to six carbon atoms,
  pyridyl, and
  pyridyl substituted with a substituent selected from the group consisting of
   halogen,
   alkyl of one to six carbon atoms, and
   alkoxy of one to six carbon atoms;
(k) naphthyl;
(l) naphthyl substituted with a substituent selected from the group consisting of
  halogen,
  alkyl of one to six carbon atoms,
  haloalkyl of one to six carbon atoms, and
  alkoxy of one to six carbon atoms;
$R^1$ and $R^2$ are independently selected from the group consisting of:
 (a) hydrogen,
 (b) alkyl of one to six carbon atoms,
 (c) halolalkyl of one to six carbon atoms,
 (d) alkoxy of one to six carbon atoms, and
 (e) halogen;
$R^3$ is selected from the group consisting of:
 (a) thienyl,
 (b) furyl,
 (c) phenyl,
 (d) naphthyl,
 (e) benzo[b]thienyl,
 (f) alkyl of one to six carbon atoms,
 (g) hydroxyl, and
 (h) hydrogen;
Y is an alkylene of one to six carbon atoms; and
M is selected from the group consisting of
 a) a pharmaceutically acceptable metabolically cleavable group,
 (b) —$OR^4$ where $R^4$ is selected from the group consisting of hydrogen and alkyl of one to six carbon atoms,
 c) —$NR^5R^6$ where $R^5$ and $R^6$ are independently selected from the group consisting of
  hydrogen,
  alkyl of one to six carbon atoms,
  hydroxy, and
  alkoxy of one to six carbon atoms,
  or $R^5$ and $R^6$ taken together define a five- to eight-membered ring, with the proviso that $R^5$ and $R^6$ may not simultaneously be hydroxyl,
 (d) —$NR^4SO_2R^7$ wherein $R^4$ is as defined above and $R^7$ is alkyl of one to six carbon atoms,
 (e) —NH-Tetrazolyl, and
 (f) glycinyl.

2. The compound according to claim 1, wherein $W^1$ and $W^2$ are independently selected at each occurrence from the group consisting of optionally substituted quinolyl, benzothiozolyl, naphthyl, and benzimidazoyl wherein the substituents are selected from the group consisting of halogen, alkyl of one to six carbon atoms, haloalkyl of one to six carbon atoms, and alkoxy of one six carbon atoms.

3. The compound according to claim 1, wherein $W^1$ and $W^2$ are at each occurrence quinolyl or quinolyl substituted with a substituent selected from the group consisting of

32 halogen, alkyl of one to six carbon atoms, haloalkyl of one to six carbon atoms, and alkoxy of one to six carbon atoms.

4. The compound according to claim 1 selected from the group consisting of:

1,1-bis(4-(2-quinolylmethoxy)phenyl)eth-1-ylthioacetic acid, (bis(4-(2-quinolylmethoxy)phenyl)-2-thienyl) methylthioacetic acid, (bis(4-(2-quinolylmethoxy)phenyl)-2-thienyl) methylthioacetic acid sodium salt, bis(4-(2-quinolylmethoxy)phenyl)methylthioacetic acid, (bis(4-(2-quinolylmethoxy)phenyl)-phenyl) methylthioacetic acid, 1,1-bis(4-(2-quinolylmethoxy)phenyl-1-pentylthioacetic acid, (bis(4-(2-quinolylmethoxy)phenyl)-furyl) methylthioacetic acid;

(4-(2-benzothiazolylmethoxy)phenyl-4-(2-quinolylmethoxy)phenyl-2-thienyl)methylthioacetic acid, (4-(6-fluoro-2-quinolylmethoxy)phenyl-4-(2-quinolylmethoxy)phenylphenyl)methylthioacetic acid, (4-(1-methyl-2-benzimidazolylmethoxy)phenyl-4-(2-quinolylmethoxy)phenyl-2-thienyl)methylthioacetic acid, (4-(2-benzothiazolylmethoxy)phenyl-4-(2-quinolylmethoxy)phenyl-2-furyl)methylthioacetic acid, 1-(4-(2-naphthylmethoxy)phenyl)-1-(4-(2-quinolylmethoxy)phenyl)-1-ethylthioacetic acid, (bis(4-(2-quinolylmethoxy)phenyl)-2-naphthyl) methylthioacetic acid, (4-(2-naphthylmethoxy)phenyl)-(4-(2-quinolylmethoxy)phenyl)-2-naphthyl)methylthioacetic acid, (2-benzo[b]thienyl-bis(4-(2-quinolylmethoxy)phenyl)) methylthioacetic acid, (2-benzo[b]thienyl-4-(1-methyl-2-benzimidazolylmethoxy)phenyl-4-(2-quinolylmethoxy)phenyl)methylthioacetic acid;

(bis(4-(2-quinolylmethoxy)phenyl)-2-thienyl)methylthio-3-propionic acid, (bis(4-(2-quinolylmethoxy)phenyl)-2-thienyl)methylthio-2-propionic acid;

4-(2-benzo[b]thienylmethoxy)phenyl-bis(4-(2-quinolylmethoxy)phenyl)methylthio-3-propionic acid, (4-(2-benzo[b]thienyl-4-(2-naphthylmethoxy)phenyl-4-(2-quinolylmethoxy)phenyl)methylthio-3-propionic acid, (bis(4-(2-quinolylmethoxy)phenyl)-2-thienyl)methylthio-2-benzoic acid, (4-(2-benzothiazolylmethoxy)phenyl-4-(2-quinolylmethoxy)phenyl)methylthio-2-benzoic acid, 1-(bis(4-(2-quinolylmethoxy)phenyl)-1-ethylthio-2-benzoic acid; and 1-(4-(2-naphthylmethoxy)phenyl-4-(2-quinolylmethoxy) phenyl)-1-ethylthio-2-benzoic acid.

5. A method for inhibiting lipoxygenase activity or leukotriene biosynthesis in a mammal in need of such treatment comprising administering to the mammal a therapeutically effective amount of a compound of claim 1.

6. A composition for inhibiting lipoxygenase activity or the biosynthesis of leukotrienes comprising a pharmaceutical carrier and a therapeutically effective amount of a compound of claim 2.

7. A composition for inhibiting lipoxygenase activity or the biosynthesis of leukotrienes comprising a pharmaceutical carrier and a therapeutically effective amount of a compound of claim 3.

8. A composition for inhibiting lipoxygenase activity or the biosynthesis of leukotrienes comprising a pharmaceutical carrier and a therapeutically effective amount of a compound of claim 4.

* * * * *